US00PP14757P2

(12) United States Plant Patent
Burchinal

(10) Patent No.: US PP14,757 P2
(45) Date of Patent: May 4, 2004

(54) APPLE TREE NAMED 'BURCHINAL RED DELICIOUS'

(50) Latin Name: *Malus domestica*
Varietal Denomination: Burchinal Red Delicious

(75) Inventor: Robert Burchinal, East Wenatchee, WA (US)

(73) Assignee: Microsoft Corporation, Redmond, WA (US)

( * ) Notice: Subject to any disclaimer, the term of this patent is extended or adjusted under 35 U.S.C. 154(b) by 0 days.

(21) Appl. No.: 10/313,685

(22) Filed: Dec. 6, 2002

(51) Int. Cl.[7] ..... A01H 5/00
(52) U.S. Cl. ..... Plt./171
(58) Field of Search ..... Plt./171

(56) References Cited

U.S. PATENT DOCUMENTS

| | | | |
|---|---|---|---|
| PP2,816 | P | 6/1968 | Trumbull |
| PP4,839 | P | 4/1982 | Evans et al. |
| PP10,832 | P | 3/1999 | Deutscher et al. |

*Primary Examiner*—Bruce R. Campell
*Assistant Examiner*—Susan B. McCormick
(74) *Attorney, Agent, or Firm*—Christensen O'Connor Johnson Kindness PLLC

(57) ABSTRACT

A new and distinct variety of apple tree which originated as a sport limb mutation of 'Wells and Wade cultivar' Oregon Spur® of red delicious apple tree (U.S. Plant Pat. No. 2,816), characterized by a more uniform deeper red color, developing much earlier than fruit of other red delicious varieties, and having a thicker stem and longer, deeper red leaf midvein.

3 Drawing Sheets

CROSS-REFERENCE TO RELATED APPLICATION

This application is a continuation of U.S. plant patent application Ser. No. 09/887,919, filed on Jun. 22, 2001 now abandoned.

Latin name of the genus and species of the plant claimed: *Malus domestica.*

Variety denomination: 'Burchinal Red Delicious'.

BACKGROUND OF THE INVENTION—DISCOVERY AND ASEXUAL REPRODUCTION OF THE TREE

The new variety, denominated 'Burchinal Red Delicious', was discovered by Robert Burchinal at the Adams Apple Orchard located at 2640 Bench Road, Othello, Wash., as a sport limb mutation. The tree having the mutated sport limb was found in a cultivated block of Oregon Spur® red delicious apple trees ('Wells & Wade cultivar'—U.S. Plant Pat. No. 2,816).

Mr. Burchinal was attracted to the tree by the sport limb that had fruit of a more uniform, deeper red color, much earlier than fruit of the remainder of the tree and neighboring trees. The new variety develops red color immediately as it comes out of bloom, as compared to other red delicious varieties, including the parent, which emerge green and gradually develop the characteristic red color. Asexual reproduction of the new variety was successfully accomplished in 1993 by budding two trees on *Malus domestica* seedling rootstock, one at Othello, Wash., and one at East Wenatchee, Wash. (second generation). Buds from the second generation trees were used in reproducing approximately 45 trees (third generation) by budding, of which approximately 9 trees of the new variety were budded in Wenatchee, Wash. The third generation trees bore fruit in 1997, identical to fruit of the parent and the discovered sport limb. In 1997, approximately 1,000 trees of the new variety were budded (fourth generation) and those trees exhibited characteristics identical to the parent, bearing fruit in fall 2001.

SUMMARY OF THE TREE

The new variety has been compared to the parent tree, Oregon Spur® ('Wells & Wade cultivar,' U.S. Plant Pat. No. 2,816), and also to Scarlet Spur® ('Snipes cultivar,' U.S. Plant Pat. No. 4,839). The new variety is similar to the parent in shape, flesh color, sugar level, and taste. However, the new variety develops an early red color at petal fall, as compared to the traditional green color of the parent and other known red delicious varieties. The leaves of the new variety have a deeper red midvein than the parent and other known varieties. Fruit and stems of the new variety exhibit a red color immediately upon emerging from bloom, and the finish color is a darker red than the finish color of the parent. The dark red color extends into the stem end of the fruit. Fruit of the new variety has a thicker stem than its parent, but of the same length, making the new variety easier to harvest.

BRIEF DESCRIPTION OF THE DRAWINGS

The accompanying photographs show the following distinguishing characteristics of this new variety.

DETAILED BOTANICAL DESCRIPTION OF THE TREE

Figure 1:
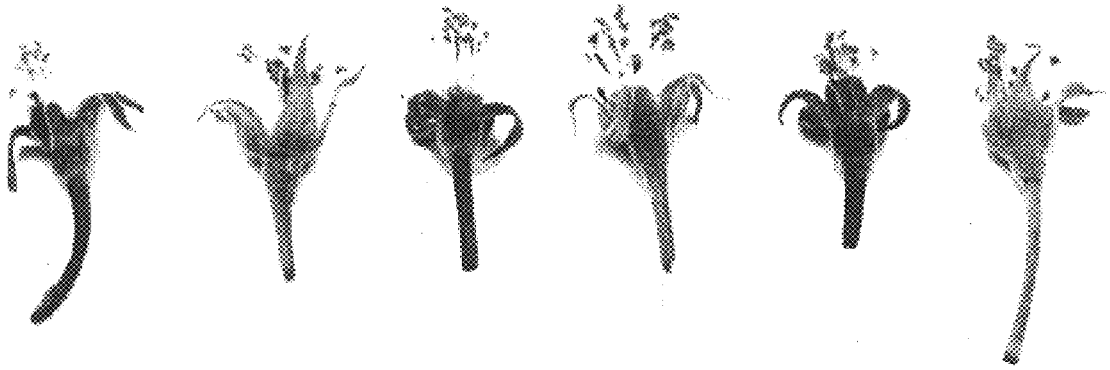
FIG. 1 shows a row of blooms after petal fall, the first, third, and fifth blooms from the left being the new variety, and the second, fourth, and sixth being from the parent, showing the deep red color of the new variety already developing as compared to the green color of the parent, and also showing the thicker developing stem of the new variety as compared to the parent, the photograph having been taken in the spring of 1998.
Figure 2:
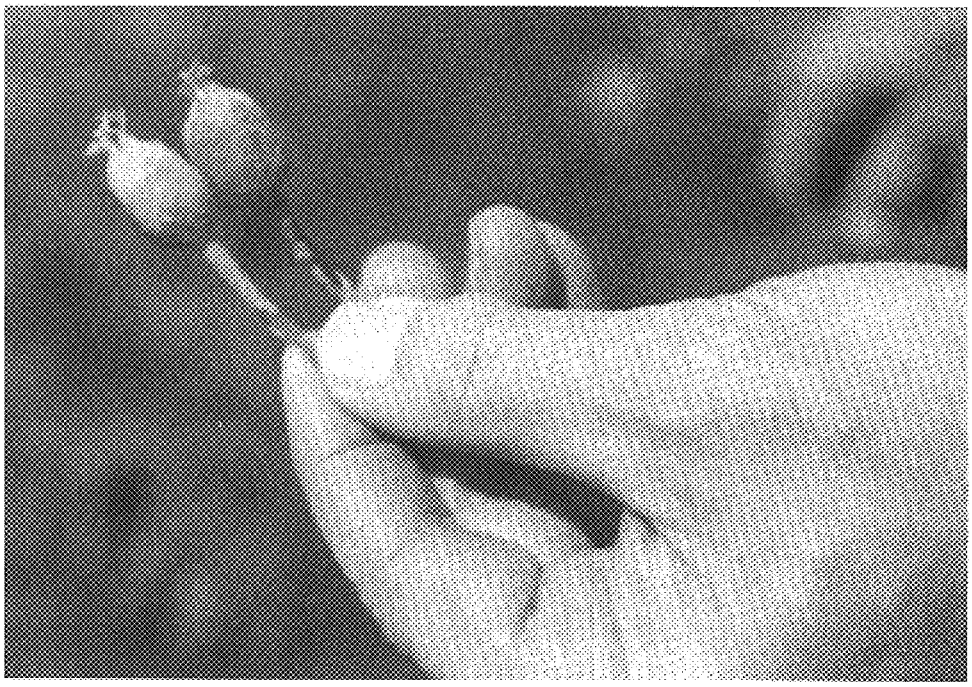
FIG. 2 shows very immature fruit of the new variety (right) as compared to fruit of the parent (left), illustrating the very early development of red color of the new variety as compared to the parent, the photograph having been taken in the spring of 1998.
Figure 3:
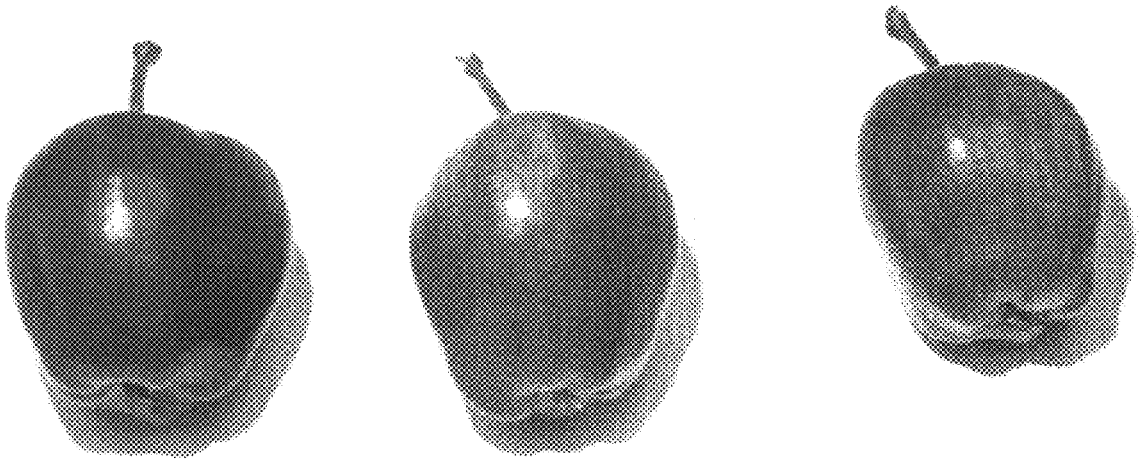
FIG. 3 shows fruit of the new variety (left) as compared to fruit of the parent Oregon Spur® (center) and fruit of Scarlet Spur® (right), illustrating the deeper red color of the new variety, the photograph having been taken on Jul. 15, 1997, approximately 10 weeks after bloom.
Figure 4:
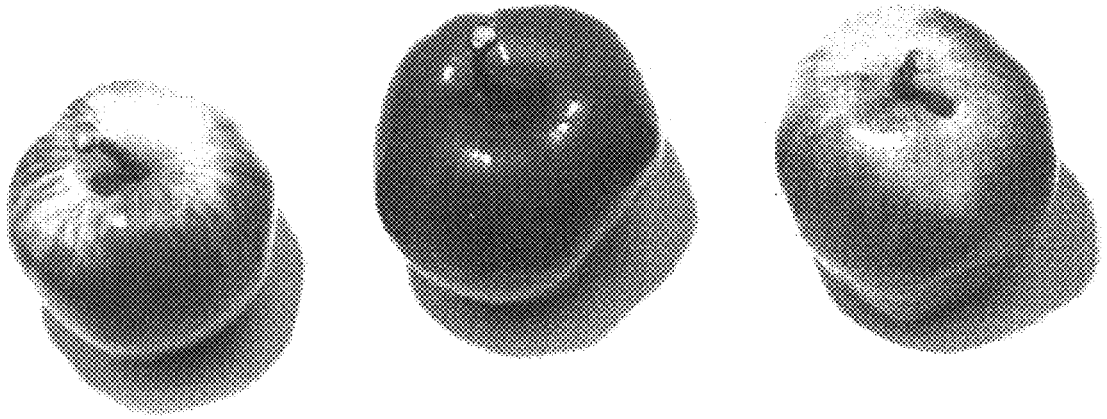
FIG. 4 is another photograph taken on Jul. 15, 1997, showing the deep red stem end of fruit of the new variety (center) as compared to fruit of the parent (right) and fruit of Scarlet Spur®.
Figure 5:
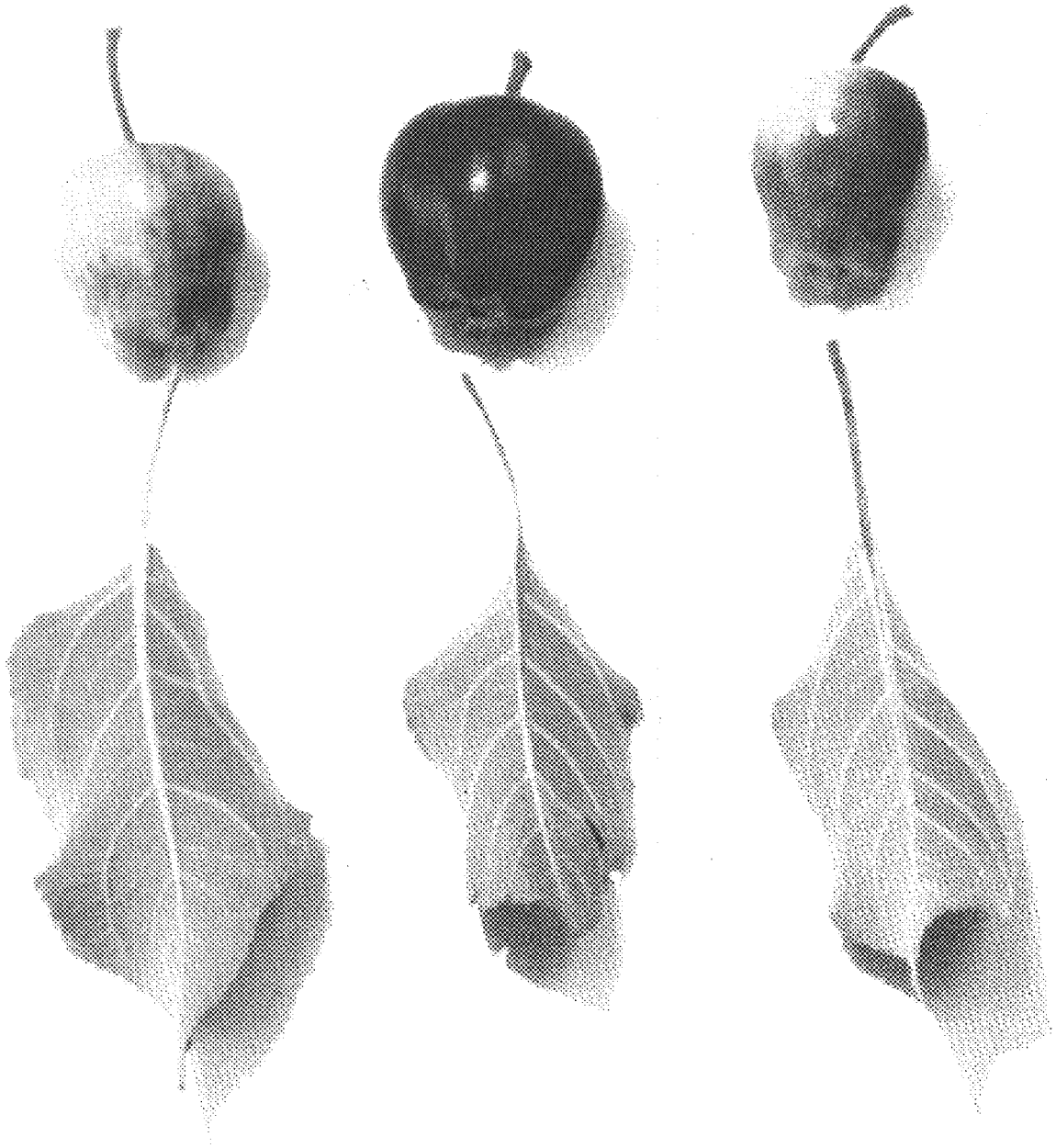
FIG. 5 shows fruit from the year 2000 crop approximately 4–6 weeks after bloom and, beneath the fruit, leaves of the associated trees, showing the early deep red color of fruit of the new variety and the red midvein of the leaf (center) as compared to fruit and leaf of the parent (right) and fruit and leaf of Scarlet Spur® (left).

Color references are to Ridgeway's *Color Standards and Color Nomenclature* unless noted otherwise.

The trees were observed on *Malus domestica* seedling rootstock at age 7, grown in Wenatchee, Wash., under North Central Washington practices as central leader trees.

Origin: Sport limb mutation of Oregon Spur® red delicious ('Wells & Wade cv.,' U.S. Plant Pat. No. 2,816) discovered at East Wenatchee, Wash., in cultivated Oregon Spur® block by Robert Burchinal.

Maturity date: September 10 to 17 at Wenatchee, Wash.

Tree:

*Medium size.*—Average height approximately 8½ feet, estimated 12 feet at maturity; Spur-type tree; Dense; Vase-formed.

*Hardy.*—Having gone through a winter of minus 15° F. without trunk damage from cold, and withstood summer heat of 105° F. without structural damage.

*Very productive.*—Normal crop load of 40 bins of fruit weighing approximately 850 pounds of fruit per bill per acre; Regular bearer; Susceptible to insects affecting red delicious trees.

*Susceptibility to diseases.*—More resistant to mildew than golden delicious or gala strains.

Trunk:

*Medium size.*—8 inches diameter at 7½ inches above the bud union; Smooth.

*Color.*—5/2 5RP (*Munsel Book of Color*).

*Trunk lenticels on four year-old trees.*—1 mm by 5 mm, light tan (5YR 8/1 — *Munsel Book of Color*).

Branches:

*Thickness.*—2 inches in circumference measured 7 inches from trunk; Smooth.

*Bark color.*—5/2 5RP (*Munsel Book of Color*); Sparse, small lenticels (1 mm diameter on two year-old wood).

Branchlets: Medium (approximately one-inch fruit spur); Short-jointed.

Flowers: Bloom from approximately April 28 to May 2 at Wenatchee, Wash., depending on the seasonal climatic conditions.

*Buds.*—Small, short, conical — plump, approximately 10 mm long by 4 mm wide, light pink (2.5R 6/10 Munsel); Blossoms are the same size, shape and color as the parent Oregon Spur: opening flower is pale pink (2.5R 7/6 Munsel) to white color with a tinge of Carmine at full bloom.

*Petals.*—Five in number, touching to overlapping, forming a corolla; Approximately 20 mm long by approximately 13 mm wide; Smooth texture; Round at apex with tapering sides to point of attachment; Sterile.

*Many clusters throughout branches.*—Large (55 mm diameter) showy blooms, 4–6 per cluster (average 5 per cluster).

*Sepals.*—Five in number, 10 mm long by 4 mm wide at base, curved downward, finely pubescent, pale green (10GY 7/2 Munsel).

*Stamen.*—Single row, bright yellow (Y-G 6.25Y Munsel) anthers, average approximately 25 to 30 per blossom.

*Pistil.*—Stiles medium (11 mm), branched at top into five elements, fused at base.

Leaf buds: Plump.

Leaves:

*Medium size.*—3 inches to 3½ inches long, 2½ inches to 2¾ inches wide; Ovate, obtuse base shape; Taper pointed, rugose; Thick; Finely serrate margins.

*Leaf arrangement.*—Alternate.

*Venation pattern.*—Alternate; Medium green leaf color (Spinach Green, Plate V, No. 29CGY, Tone M); Red midvein (Acajou Red, Plate XIII, No. 1 Red, Tone I).

*Petiole.*—Medium length (⅝" to ¾"), slender; (2 mm diameter at base), light green upper surface (2.5GY 6/4 — *Munsel Book of Color*); Purple lower surface (2.5R 3/8 — *Munsel Book of Color*).

Fruit (average of three apples harvested Sep. 25, 2001, unless noted otherwise): large (3¼" length, 3" width, on young trees).

*Average weight.*—8 ounces (average of 10 apples from year 2002 harvest); Uniform, conical, symmetrical, prominent crowning at distal end with conspicuous lobes.

*Length of season.*—135 to 145 days.

*Maturity for picking in North Central Washington.*—September 20 to October 1 for the 2001 season based on soluble solids of 12 to 14 brix; Hangs well.

*Keeping quality.*—Good.

*Shipping quality.*—Good, Susceptible to insects affecting red delicious.

*Stem.*—Medium (1" length, ⅛" thick).

*Stem color.*—Indian Purple Plate XXXVIII No. 67VR, Tone M.

*Stem cavity.*—Medium depth (1.7 cm from plane of shoulders to base of stem), broad (3.5 cm between shoulders), smooth, symmetrical.

*Calyx.*—Closed, medium depth (1.8 cm from plane of lobes to base of basin cavity), medium breadth (3.4 cm from lobe to lobe center).

*Skin.*—Smooth, waxy, glossy.

*Locules (carpels).*—Small (1.7 cm diameter), 5 in number, narrow, generally slightly open.

*Finish color.*—Indian Purple (blush coloring) Plate XXXVIII No. 67VR, Tone M.

*Lenticels.*—Small (0.5 to 1.0 mm), not numerous (approximately 6 per square cm), conspicuous, round; color: Pale Pinkish Buff, Plate XXIX No. 17O-Y, Tone F.

*Flesh.*—Yellow tinged, fine, crisp, juicy, sweet, aromatic.

*Flesh color.*—Between Marguerite Yellow and Ivory Yellow.

*Core.*—Medium size (3.5 cm width by 3.0 cm length), closed carpel.

*Core lines.*—Meeting.

*Calyx tube.*—Medium (±1 cm), funnel shaped, typically closed.

*Seeds.*—Usually two per cell, medium size (5/16" length, 1/8" to 3/16" width), plump, obtuse point.

*Seed color.*—Burnt Umber Plate XXVIII, No. 9, Tone M.

*Use.*—Dessert.

I claim:

1. A new and distinct variety of apple tree substantially as herein shown and described.

* * * * *

UNITED STATES PATENT AND TRADEMARK OFFICE

CERTIFICATE OF CORRECTION

PATENT NO. : PP 14,757 P2
DATED : May 4, 2004
INVENTOR(S) : R. Burchinal

It is certified that error appears in the above-identified patent and that said Letters Patent is hereby corrected as shown below:

Title page,
Item [73], Assignee, delete "[73] Assignee: Microsoft Corporation, Redmond, WA (US)"

Signed and Sealed this

Fifteenth Day of February, 2005

JON W. DUDAS
*Director of the United States Patent and Trademark Office*